(12) United States Patent
Okumura et al.

(10) Patent No.: US 11,073,645 B2
(45) Date of Patent: Jul. 27, 2021

(54) TEMPERATURE SENSOR

(71) Applicant: NITTO DENKO CORPORATION, Osaka (JP)

(72) Inventors: Keisuke Okumura, Osaka (JP); Ryoma Yoshioka, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 86 days.

(21) Appl. No.: 16/087,942

(22) PCT Filed: Feb. 3, 2017

(86) PCT No.: PCT/JP2017/004008
§ 371 (c)(1),
(2) Date: Sep. 24, 2018

(87) PCT Pub. No.: WO2017/169109
PCT Pub. Date: Oct. 5, 2017

(65) Prior Publication Data
US 2019/0346602 A1 Nov. 14, 2019

(30) Foreign Application Priority Data
Mar. 30, 2016 (JP) .............................. JP2016-067471

(51) Int. Cl.
G02B 5/28 (2006.01)
G02B 26/02 (2006.01)
(Continued)

(52) U.S. Cl.
CPC ............... *G02B 5/28* (2013.01); *G02B 26/02* (2013.01); *H01L 31/048* (2013.01); *H01L 31/0445* (2014.12)

(58) Field of Classification Search
CPC ...... G02B 13/0045; G02B 9/60; G02B 13/04; G02B 7/021; G02B 5/28; G02B 26/02;
(Continued)

(56) References Cited

U.S. PATENT DOCUMENTS

2008/0190138 A1 8/2008 DiCiacco et al.
2010/0245112 A1* 9/2010 Ludwig ..................... G09F 9/30
235/492

(Continued)

FOREIGN PATENT DOCUMENTS

CN 101802890 A 8/2010
CN 201780163 U 3/2011
(Continued)

OTHER PUBLICATIONS

International Preliminary Report on Patentability issued by WIPO dated Oct. 2, 2018, in connection with International Patent Application No. PCT/JP2017/004008.
(Continued)

*Primary Examiner* — Mohammed A Hasan
(74) *Attorney, Agent, or Firm* — Edwards Neils LLC; Jean C. Edwards, Esq.

(57) ABSTRACT

A temperature sensor includes a solar cell, and a thermochromic resin covering the solar cell and having a light transmittance changeable according to a temperature change.

8 Claims, 3 Drawing Sheets

(51) Int. Cl.
*H01L 31/0445* (2014.01)
*H01L 31/048* (2014.01)

(58) Field of Classification Search
CPC . H04N 5/2254; H01L 31/0445; H01L 31/048; H01L 31/02164; H01L 31/054; G01K 11/14; G01K 13/20; G01K 3/005; G01K 11/16; A61B 5/01; A61B 5/6833; Y02E 10/50; Y02E 10/52
USPC .......................................................... 359/738
See application file for complete search history.

(56) References Cited

U.S. PATENT DOCUMENTS

| | | | |
|---|---|---|---|
| 2012/0160297 | A1 | 6/2012 | Yamakawa et al. |
| 2012/0263209 | A1* | 10/2012 | Panda ...................... G01K 7/00 374/163 |
| 2012/0298200 | A1* | 11/2012 | Niggemann .......... H01L 27/301 136/258 |
| 2015/0171247 | A1* | 6/2015 | Maruko ................... C09K 3/10 136/259 |
| 2015/0286073 | A1* | 10/2015 | Blum ...................... G02C 7/102 351/159.66 |
| 2017/0373207 | A1* | 12/2017 | Hwang ............... H01L 31/0516 |

FOREIGN PATENT DOCUMENTS

| | | |
|---|---|---|
| CN | 104409541 A | 3/2015 |
| CN | 204314562 U | 5/2015 |
| EP | 3437690 A1 | 2/2019 |
| JP | 56-011328 A | 2/1981 |
| JP | S61-048333 U | 4/1986 |
| JP | S61-072654 U | 5/1986 |
| JP | H01-203926 A | 8/1989 |
| JP | H07-280663 A | 10/1995 |
| JP | 2010-239045 A | 10/2010 |
| JP | 2015-060885 A | 3/2015 |
| KR | 10-2013-0074631 A | 7/2013 |

OTHER PUBLICATIONS

Office Action, issued by the Japanese Patent Office dated Nov. 19, 2019, in connection with Japanese Patent Application No. 2016-067471.
International Search Report Issued in PCT/JP2017/004008 dated Apr. 4, 2017.
Written Opinion Issued in PCT/JP2017/004008 dated Apr. 4, 2017.
Chinese Office Action issued by the China National Intellectual Property Administration dated Mar. 4, 2020 in connectio with Chinese Patent Application No. 201780021279.3.
Extended European Search Report issued by the European Patent Office dated Oct. 18, 2019, in connection with European Patent Application No. 17773658.4.
Office Action, issued by the European Patent Office dated Jul. 24, 2020, in connection with European Patent Application No. 17773658.4.
Office Action, which was issued by the China National Intellectual Property Administration dated Aug. 27, 2020, in connection with Chinese Patent Application No. 201780021279.3.
Office Action, which was issued by the China National Intellectual Property Administration dated Dec. 2, 2020, in connection with Chinese Patent Application No. 201780021279.3.
Office Action, issued by the European Patent Office dated Feb. 18, 2021, in connection with European Patent Application No. 17773658.4.

* cited by examiner

TEMPERATURE SENSOR

CROSS-REFERENCE TO RELATED APPLICATIONS

The present application is a 35 U.S.C. 371 National Stage Entry of PCT/JP2017/004008, filed on Feb. 3, 2017, which claims priority from Japanese Patent Application No. 2016-067471, filed on Mar. 30, 2016, the contents of all of which are herein incorporated by reference in their entirety.

TECHNICAL FIELD

The present invention relates to a temperature sensor, to be specific, to a temperature sensor used in various industries.

BACKGROUND ART

Conventionally, it has been known that an automatic fire alarm facility includes a sensor.

As such a sensor, for example, a thermosensitive sensor including a light emitting diode and a light-receiving transistor that are disposed at spaced intervals to each other, a thermosensitive transparentized sheet that is disposed therebetween, and a power source that is constantly connected to the light emitting diode has been known (ref: for example, Patent Document 1).

In the thermosensitive sensor of Patent Document 1, the thermosensitive transparentized sheet is cloudy at a normal temperature, and by being transparentized by heating, light emitted from the light emitting diode transmits the thermosensitive transparentized sheet to reach the light-receiving transistor to then drive it.

CITATION LIST

Patent Document

Patent Document 1: Japanese Unexamined Patent Application No. H7-280663

SUMMARY OF THE INVENTION

Problem to be Solved by the Invention

The thermosensitive sensor described in Patent Document 1 is required to include a power source so as to allow the light emitting diode to emit light. Thus, there is a disadvantage that in the thermosensitive sensor described in Patent Document 1, the number of components increases, and the device structure becomes complicated.

An object of the present invention is to provide a temperature sensor having a reduced number of components and having a simple device structure without including a power source.

Means for Solving the Problem

The present invention [1] includes a temperature sensor including a solar cell, and a thermochromic resin covering the solar cell and having a light transmittance changeable according to a temperature change.

When the temperature sensor is disposed under the environment of being exposed to light, and the temperature of the thermochromic resin changes based on a temperature change of the environment, the light transmittance of the thermochromic resin increases. Then, the light transmits the thermochromic resin, subsequently, the solar cell receives the light to generate an electromotive force, and the temperature change of the environment can be detected by the electromotive force.

The temperature sensor detects the temperature change of the environment based on the electromotive force of the solar cell because of an increase in the light transmittance of the thermochromic resin, so that it is not necessary to separately provide a power source as in Patent Document 1. Thus, in the temperature sensor, the number of components is reduced, and the device structure is simple.

The present invention [2] includes the temperature sensor described in [1], wherein the thermochromic resin is in direct contact with the solar cell.

In the temperature sensor, the thermochromic resin is in direct contact with the solar cell, so that the solar cell can directly receive the light transmitting the thermochromic resin. Thus, the temperature change of the environment can be detected with excellent sensitivity.

The present invention [3] includes the temperature sensor described in [1] or [2], wherein each of the thermochromic resin and the solar cell has a film shape, and the thermochromic resin is disposed at one side in a thickness direction of the solar cell.

The temperature sensor includes the solar cell having a film shape, and the thermochromic resin disposed at one side in the thickness direction thereof and having a film shape, so that the structure is simple, and the miniaturization thereof can be achieved.

The present invention [4] includes the temperature sensor described in any one of [1] to [3] further including an electric power detecting portion electrically connected to the solar cell and detecting an electromotive force generated in the solar cell.

According to the temperature sensor, the electric power detecting portion detects the electromotive force generated in the solar cell, so that the temperature change of the environment can be surely detected.

The present invention [5] includes the temperature sensor described in [4], wherein the electric power detecting portion is operated by an electric power directly supplied from the solar cell.

In the temperature sensor, the electric power detecting portion is operated by the electric power directly supplied from the solar cell, so that the temperature sensor can be driven without separately providing an external power source in the temperature sensor. Thus, in the temperature sensor, the number of components is reduced, and the device structure is simple.

The present invention [6] includes the temperature sensor described in [4] or [5] further including a transmitting device connected to the solar cell, wherein the electric power detecting portion is the transmitting device.

In the temperature sensor, the electric power detecting portion is the transmitting device connected to the solar cell, so that the temperature change of the environment can be surely detected remotely based on the signal transmitted from the electric power detecting portion.

Effect of the Invention

In the temperature sensor of the present invention, the number of components is reduced, and the device structure is simple.

DESCRIPTION OF EMBODIMENTS

1. First Embodiment

Figure 1:
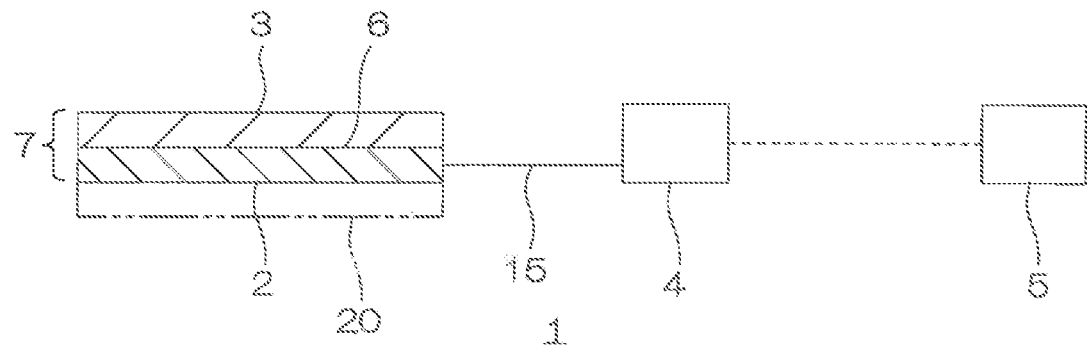
FIG. 1 shows a schematic view of a first embodiment of a temperature sensor of the present invention.

As shown in FIG. 1, a temperature sensor 1 includes a solar cell layer 2 as one example of a solar cell, a thermochromic resin layer 3 as one example of a thermochromic resin, and a transmitter 4 as one example of a transmitting device. Also, the temperature sensor 1 further includes a receiver 5.

1-1. Solar Cell Layer

The solar cell layer 2 is, for example, a solar cell made of a crystalline or amorphous silicon or the like. The solar cell layer 2 has a film shape. The solar cell layer 2 has a light receiving surface (main surface) 6 for generating an electromotive force by receiving light on the upper surface thereof. The solar cell layer 2 is a one surface-type solar cell that generates the electromotive force by receiving the light from the light receiving surface 6.

1-2. Thermochromic Resin Layer

The thermochromic resin layer 3 is disposed on the entire light receiving surface 6 of the solar cell layer 2. In this manner, the thermochromic resin layer 3 covers the solar cell layer 2. The thermochromic resin layer 3 is in direct contact with the light receiving surface 6 of the solar cell layer 2. The thermochromic resin layer 3 has a film shape. The thermochromic resin layer 3 constitutes a sensor laminate 7 along with the solar cell layer 2. The sensor laminate 7 includes the solar cell layer 2 and the thermochromic resin layer 3. Preferably, the sensor laminate 7 is made of only the solar cell layer 2 and the thermochromic resin layer 3.

The thermochromic resin layer 3 is formed from a resin composition having thermochromic properties into a film shape.

The resin composition contains, for example, a resin and a thermochromic material. Examples of the resin include transparent resins such as silicone resin, epoxy resin, and acrylic resin. An example of the thermochromic material includes a thermochromic pigment. An example of the thermochromic pigment includes a heat sensitive material in which three components of an electron donative coloring organic compound, a compound having a phenolic hydroxyl group, and a compound having an alcoholic hydroxyl group are contained as an essential component (Japanese Examined Patent Publications No. S51-44706, No. S51-44707, No. H1-29398, or the like). The thermochromic material is a reversible thermochromic composition that changes its color before or after a predetermined temperature T (color changing point), is brought into a discoloring (colorless) state in a temperature region of a higher temperature-side color changing point or more, and is brought into a coloring (colored) state in a temperature region of below a lower temperature-side color changing point. To be specific, an example thereof includes a heat sensitive material (Example 4 of Japanese Examined Patent Publication No. S51-44706) that is made of crystal violet lactone (electron donative coloring organic compound), propyl ester gallate (compound having a phenolic hydroxyl group), and n-myristyl alcohol (compound having an alcoholic hydroxyl group), and its color changing point is 35° C. Also, an example thereof includes a heat sensitive material (Example 23 of Japanese Examined Patent Publication No. S51-44706) that is made of crystal violet lactone (electron donative coloring organic compound), isooctyl gallate (compound having a phenolic hydroxyl group), and n-melissyl alcohol (compound having an alcoholic hydroxyl group), and its color changing point is 97° C. The mixing ratio of the thermochromic material with respect to 100 parts by mass of the resin is, for example, 1 part by mass or more, preferably 3 parts by mass or more, and for example, 25 parts by mass or less, preferably 15 parts by mass or less.

Thus, the thermochromic resin layer 3 has properties (thermochromic properties) of showing a thermochromic phenomenon in which a light transmittance reversibly changes in accordance with the temperature change. To be more specific, at below the temperature T (° C.), the thermochromic resin layer 3 has a low light transmittance, for example, depends on the illuminance of light applied to the thermochromic resin layer 3, and has a light transmittance that does not generate an electromotive force in the solar cell layer 2 when a part of the light transmits the thermochromic resin layer 3. Meanwhile, at the temperature T (° C.) or more, the thermochromic resin layer 3 has a high light transmittance, for example, depends on the illuminance of light applied to the thermochromic resin layer 3, and has a light transmittance that generates an electromotive force in the solar cell layer 2 when the light transmits the thermochromic resin layer 3.

To be specific, the ratio (T2/T1) of a light transmittance T2 of the thermochromic resin layer 3 at the temperature T (° C.) (color changing point of the thermochromic material) or more to a light transmittance T1 of the thermochromic resin layer 3 at below the temperature T (° C.) (color changing point of the thermochromic material) is, for example, above 1.00, preferably 1.05 or more, more preferably 1.20 or more, further more preferably 1.50 or more. The light transmittance is a transmittance of visible light (400 to 700 nm). The light transmittance is measured with CM-700d manufactured by Konica Minolta, Inc. The light transmittance at the temperature T is a light transmittance that allows the transmission of the minimum light necessary for generation of the electromotive force of the solar cell layer 2.

The above-described temperature T is appropriately determined in accordance with the environment in which the temperature sensor 1 is disposed, and appropriately selected in accordance with the type of the thermochromic material. To be specific, the temperature T is, for example, −20° C. or more, preferably 0° C. or more, more preferably 20° C. or more, and for example, 150° C. or less, preferably 130° C. or less.

The thickness of the thermochromic resin layer 3 is, for example, 5 μm or more, preferably 25 μm or more, and for example, 1000 μm or less, preferably 250 μm or less.

1-3. Transmitter

The transmitter 4 is electrically connected to the solar cell layer 2. To be specific, the transmitter 4 is connected to the solar cell layer 2 via a first wire 15. The transmitter 4 is an electric power detecting portion 4 that detects an electromotive force generated in the solar cell layer 2. To be specific, the transmitter 4 is constituted to detect the electromotive force generated in the solar cell layer 2, and to wirelessly transmit a detected signal to the receiver 5 by using the electromotive force as an electric power. That is, the transmitter 4 is operated by the electric power directly supplied from the solar cell layer 2. The transmitter 4 includes, for example, a transmitting antenna (not shown) capable of wirelessly transmitting a detected signal.

1-4. Receiver

The receiver 5 is disposed in a remote position with respect to the transmitter 4.

The receiver 5 includes, for example, a receiving antenna (not shown) capable of receiving a detected signal wirelessly transmitted from the transmitter 4, an amplifier (not shown) that amplifies the detected signal received by the receiving antenna, and a display device (not shown) that displays whether or not the temperature of the environment in which the sensor laminate 7 is disposed is the temperature T (color changing point of the thermochromic material) or more based on the detected signal that is amplified.

2. Use and Detection Method

The temperature sensor 1 can be used as a temperature sensor of various industries. The temperature sensor 1 is placed in the environment of being exposed to light such as natural light including sunlight, and illumination light based on indoor lighting.

To be specific, the temperature sensor 1 is, for example, provided as an atmospheric temperature sensor in an automatic fire alarm facility and an air conditioning facility. The temperature sensor 1 is also, for example, provided in a patch (adhesive skin patch, patch preparation), an excessive temperature rise warning facility provided in the environment difficult to access for human beings (for example, under the presence of a poisonous gas, high place, place requiring trouble in cell change and place difficult for wire connection, or the like), and clothing (clothes, hat, and shoe) at the time of outdoor work so as to prevent heat stroke.

2-1. Air Conditioning Facility

When the temperature sensor 1 is provided in the air conditioning facility, for example, the sensor laminate 7 and the transmitter 4 are placed in a place requiring air conditioning (detecting place). Meanwhile, the receiver 5 is connected to a switch of the air conditioning facility. Examples of the air conditioning facility include a heating facility (for example, heating facility that heats a structure used in cultivation in greenhouse (what is called plastic greenhouse)) and a cooling facility.

Next, a detection method in a case where the temperature sensor 1 is provided in the heating facility is described.

When the atmospheric temperature at the detecting place is low (in the case of below the temperature T (color changing point of the thermochromic material)), the temperature sensor 1 shields light to the solar cell layer 2 because of the low light transmittance of the thermochromic resin layer 3. Thus, the solar cell layer 2 does not generate an electromotive force, the transmitter 4 does not transmit a signal, and the receiver 5 does not receive the signal. The heating facility continuously heats the inside of the detecting place (structure).

Meanwhile, when the atmospheric temperature at the detecting place is high (in the case of the temperature T (color changing point of the thermochromic material) or more), the temperature of the thermochromic resin layer 3 is high, then, the light transmittance of the thermochromic resin layer 3 is high, and the solar cell layer 2 receives light via the thermochromic resin layer 3. Then, the solar cell layer 2 generates an electromotive force, the transmitter 4 transmits a signal based on the electromotive force of the solar cell layer 2, and the receiver 5 receives the signal. In this manner, the switch of the heating facility is turned off, and the heating of the inside of the structure is interrupted (stopped). While the atmospheric temperature of the detecting place is the temperature T or more, the generation of the electromotive force by the solar cell layer 2, the transmission of the signal by the transmitter 4, and the reception of the signal by the receiver 5 continue.

Thereafter, when the atmospheric temperature of the detecting place is low again (in the case of being brought back to below the temperature T (color changing point of the thermochromic material), the light transmittance of the thermochromic resin layer 3 is low, so that the thermochromic resin layer 3 shields the light. Thus, the solar cell layer 2 does not generate an electromotive force, the transmitter 4 stops the transmission of a signal, and the receiver 5 does not receive the signal. As a result, the switch of the heating facility is turned on, and the heating of the inside of the structure starts again.

2-2. Automatic Fire Alarm Facility

When the temperature sensor 1 is provided in the automatic fire alarm facility, the sensor laminate 7 and the transmitter 4 are placed in a place requiring the detection of a fire (detecting place). Meanwhile, the receiver 5 is provided in a management facility such as disaster control center.

The temperature sensor 1 is under the normal temperature environment, and the temperature of the thermochromic resin layer 3 is usually low (below the temperature T (color changing point of the thermochromic material)), so that the light transmittance of the thermochromic resin layer 3 is low. Thus, the light to the solar cell layer 2 is shielded. Thus, the solar cell layer 2 does not generate an electromotive force, the transmitter 4 does not transmit a fire signal, and the receiver 5 does not receive the fire signal.

Meanwhile, when a fire breaks out, the temperature of the thermochromic resin layer 3 is high (the temperature T (color changing point of the thermochromic material) or more), so that the light transmittance of the thermochromic resin layer 3 is high, the light transmits the thermochromic resin layer 3, and the solar cell layer 2 receives the light via the thermochromic resin layer 3. Then, the solar cell layer 2 generates an electromotive force, the transmitter 4 transmits a fire signal based on the electromotive force of the solar cell layer 2, and the receiver 5 receives the fire signal.

2-3. Patch

When the temperature sensor 1 is used in the patch, the sensor laminate 7 is laminated on the patch. To be specific, the rear surface (surface opposite to the light receiving surface 6) of the solar cell layer 2 is laminated on a patch layer 20 (ref: phantom line of FIG. 1). The patch layer 20 contains a patch medicinal component, has pressure-sensitive adhesive properties, and has a sheet shape. That is, a patch laminate that sequentially includes the patch layer 20, the solar cell layer 2, and the thermochromic resin layer 3 in a thickness direction is prepared. The transmitter 4 is disposed in the neighborhood of the patch layer 20. Meanwhile, the receiver 5 is disposed so as to be managed by a medical administrator.

The patch is not in contact with a human body before it is administered thereto, so that the temperature of the thermochromic resin layer 3 is low (below the temperature T (color changing point of the thermochromic material)), the light transmittance of the thermochromic resin layer 3 is low, and the thermochromic resin layer 3 shields the light to the solar cell layer 2. Thus, the solar cell layer 2 does not generate an electromotive force, the transmitter 4 does not transmit a signal (patch signal) of sticking the patch to the human body, and the receiver 5 does not receive the signal (patch signal).

Next, when a patched surface of the patch layer 20 is stuck to the human body, a heat from the human body is conducted to the thermochromic resin layer 3 via the patch layer 20 and the solar cell layer 2. Then, the temperature of the thermochromic resin layer 3 is high (the temperature T (color changing point of the thermochromic material) or more), so that the light transmittance of the thermochromic resin layer 3 is high, and the solar cell layer 2 receives the light via the thermochromic resin layer 3. Then, the solar cell layer 2 generates an electromotive force, the transmitter 4 transmits a patch signal based on the electromotive force of the solar cell layer 2, and the receiver 5 receives the patch signal. The medical administrator recognizes the patch signal in the receiver 5.

3. Function and Effect

When the temperature sensor 1 is disposed under the environment of being exposed to the light, and the temperature of the thermochromic resin layer 3 changes based on the temperature change of the environment, the light transmittance of the thermochromic resin layer 3 increases. Then, the light transmits the thermochromic resin layer 3, subsequently, the solar cell layer 2 receives the light to generate the electromotive force, and the temperature change of the environment can be detected by the electromotive force.

The temperature sensor 1 detects the temperature change of the environment based on the electromotive force of the solar cell layer 2 because of an increase in the light transmittance of the thermochromic resin layer 3, so that it is not necessary to separately provide a power source as in Patent Document 1. Thus, in the temperature sensor 1, the number of components is reduced, and the device structure is simple.

In the temperature sensor 1, the thermochromic resin layer 3 is in direct contact with the solar cell layer 2, so that the solar cell layer 2 can directly receive the light transmitting the thermochromic resin layer 3. Thus, the temperature change of the environment can be detected with excellent sensitivity.

The temperature sensor 1 includes the solar cell layer 2 having a film shape, and the thermochromic resin layer 3 disposed at one side in the thickness direction thereof and having a film shape, so that the structure is simple, and the miniaturization thereof can be achieved.

According to the temperature sensor 1, the transmitter 4 that is an electric power detecting portion detects the electromotive force generated in the solar cell layer 2, so that the temperature change of the environment can be surely detected.

In the temperature sensor 1, the transmitter 4 is operated by the electric power directly supplied from the solar cell layer 2, so that the transmitter 4 can be driven without separately providing an external power source in the temperature sensor 1. Thus, in the temperature sensor 1, the number of components is reduced, and the device structure is simple.

In the temperature sensor 1, the electric power detecting portion is the transmitter 4 connected to the solar cell layer 2, so that the temperature change of the environment can be surely detected remotely by allowing the receiver 5 to receive the signal transmitted from the transmitter 4.

4. Modified Example of First Embodiment

In the first embodiment, as shown in FIG. 1, the temperature sensor 1 includes the receiver 5.

Alternatively, though not shown, the temperature sensor 1 may be constituted without including the receiver 5.

That is, the temperature sensor 1 includes the solar cell layer 2, the thermochromic resin layer 3, and the transmitter 4. Meanwhile, the receiver 5 is provided in a receiving device (not shown) that is provided separately from the temperature sensor 1.

In the first embodiment, each of the solar cell layer 2 and the thermochromic resin layer 3 has a film shape.

Alternatively, at least one of the solar cell layer 2 and the thermochromic resin layer 3 may not have a film shape, and have, for example, an indefinite shape (excluding a film shape) such as a block shape.

In the first embodiment, the thermochromic resin layer 3 shields the light to the solar cell layer 2 at below the temperature T (color changing point of the thermochromic material). Alternatively, a part of the light may transmit the thermochromic resin layer 3, and the solar cell layer 2 may generate a first electromotive force. In such a case, the entire light or a part thereof transmits the thermochromic resin layer 3, the solar cell layer 2 generates a second electromotive force, and the transmitter 4 transmits a patch signal based on a difference between the two electromotive forces (second electromotive force—first electromotive force, that is, increase in the electromotive force) at the temperature T (color changing point of the thermochromic material) or more.

5. Second Embodiment

In the second embodiment, the same reference numerals are provided for members and steps corresponding to each of those in the first embodiment, and their detailed description is omitted.

In the first embodiment, as shown in FIG. 1, the thermochromic resin layer 3 is in direct contact with the solar cell layer 2.

Figure 2:
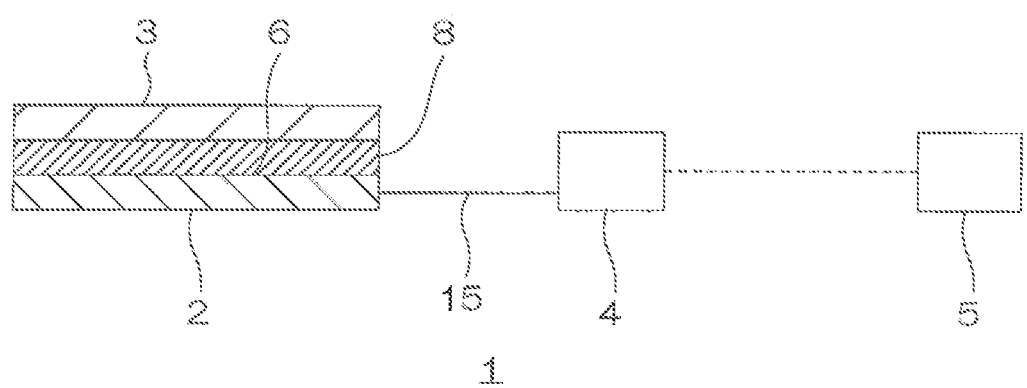
FIG. 2 shows a schematic view of a second embodiment of a temperature sensor of the present invention.

Meanwhile, in the second embodiment, as shown in FIG. 2, the thermochromic resin layer 3 is laminated in the solar cell layer 2 via a functional layer 8. The sensor laminate 7 sequentially includes the solar cell layer 2, the functional layer 8, and the thermochromic resin layer 3 in the thickness direction.

The functional layer 8 covers the light receiving surface 6 of the solar cell layer 2. To be specific, the functional layer 8 is disposed on the light receiving surface 6 of the solar cell layer 2. The functional layer 8 has a film shape.

Examples of the functional layer 8 include heat insulating layer, specific wavelength transmitting layer, adhesive layer, and substrate layer.

5-1. Heat Insulating Layer

The heating insulating layer is made of a transparent heat insulating material. Examples of the heat insulating material include foaming polyolefins such as foaming polyethylene and foaming polypropylene; foaming polystyrene; resin foams such as foaming polyurethane; resin sheets added with a hollow silica; and silica aerogels. The thickness of the heat insulating layer is, for example, 5 μm or more, and for example, 1000 μm or less.

When the functional layer 8 is the heat insulating layer, for example, in a case where the temperature sensor 1 is used in the patch, the heat conduction to the thermochromic resin layer 3 with respect to the human body can be slowed. Accordingly, for example, when the human body touches the patch layer 20 by accident, the heat conduction to the thermochromic resin layer 3 based on the touch of a finger is slowed, and as a result, a change of the light transmittance of the thermochromic resin layer 3 can be prevented. That is, the malfunction of the temperature sensor 1 at the time of the touch of the human body to the patch layer 20 by accident can be prevented.

5-2. Specific Wavelength Transmitting Layer

The specific wavelength transmitting layer is made of a material in which only the light of the specific wavelength can transmit, and the light other than the light of the specific wavelength can be shielded. The thickness of the specific wavelength transmitting layer is, for example, 5 μm or more, and for example, 250 μm or less.

When the functional layer 8 is the specific wavelength transmitting layer, of the light entering the solar cell layer 2, only the light of the specific wavelength can transmit. Thus, the light that cannot be shielded by the thermochromic resin layer 3 (for example, infrared wavelength of the sunlight) can be shielded, and the malfunction at the time of the temperature below the color changing point (T) can be prevented.

5-3. Adhesive Layer

The adhesive layer is made of a transparent adhesive material. The thickness of the adhesive layer is, for example, 5 μm or more, and for example, 250 μm or less.

When the functional layer 8 is the adhesive layer, even in a case where the thermochromic resin layer 3 does not have adhesive properties (pressure-sensitive adhesive properties), the thermochromic resin layer 3 can be stuck to the solar cell layer 2. Thus, the reliability of the sensor laminate 7, and accordingly, the reliability of the temperature sensor 1 can be improved.

5-4. Substrate Layer

The substrate layer is, for example, made of a transparent hard material such as glass substrate. The thickness of the substrate layer is, for example, 25 μm or more, and for example, 1000 μm or less.

When the functional layer 8 is the substrate layer, the solar cell layer 2 and the thermochromic resin layer 3 can be supported by the functional layer 8. Thus, the mechanical strength of the sensor laminate 7 can be improved.

The thermochromic resin layer 3 covers the surface (upper surface) of the functional layer 8. The thermochromic resin layer 3 is disposed on the surface (upper surface) of the functional layer 8.

According to the second embodiment, as shown in FIG. 2, each of the functions and effects described above based on the functional layer 8 can be achieved.

Meanwhile, in the first embodiment, as shown in FIG. 1, the thermochromic resin layer 3 is in direct contact with the solar cell layer 2, so that the solar cell layer 2 can directly receive the light transmitting the thermochromic resin layer 3. Thus, the temperature change of the environment can be detected with excellent sensitivity.

6. Third Embodiment

In the third embodiment, the same reference numerals are provided for members and steps corresponding to each of those in the first and second embodiments, and their detailed description is omitted.

In the first embodiment, as shown in FIG. 1, the thermochromic resin layer 3 is disposed only at one side in the thickness direction (upper side in FIG. 1) of the solar cell layer 2.

Figure 3:
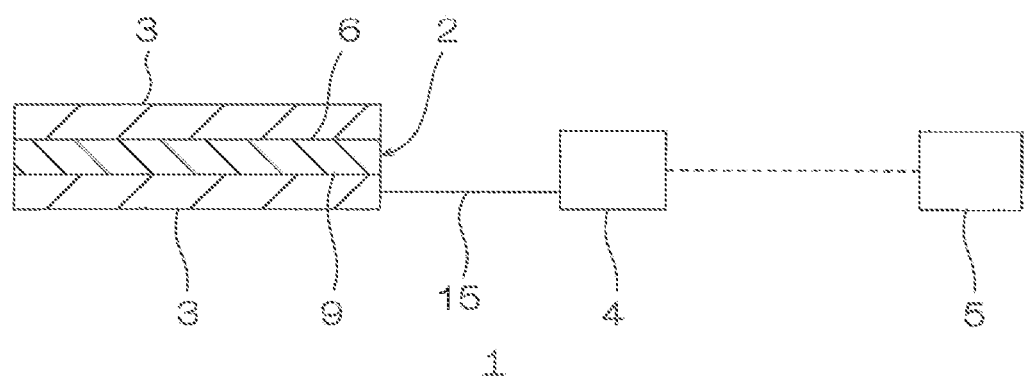
FIG. 3 shows a schematic view of a third embodiment of a temperature sensor of the present invention.

Meanwhile, in the third embodiment, as shown in FIG. 3, the thermochromic resin layer 3 is disposed at both sides in the thickness direction of the solar cell layer 2.

The solar cell layer 2 has a first light receiving surface (first main surface) 6 and a second light receiving surface (second main surface) 9 that face each other in the thickness direction. The solar cell layer 2 can generate an electromotive force based on the light received at both surfaces (two main surfaces) of the first light receiving surface 6 and the second light receiving surface 9. In short, the solar cell layer 2 is a double surface-type solar cell.

The thermochromic resin layer 3 is laminated on both surfaces of the first light receiving surface 6 and the second light receiving surface 9 of the solar cell layer 2. The thermochromic resin layer 3 is in direct contact with both surfaces of the first light receiving surface 6 and the second light receiving surface 9 of the solar cell layer 2.

Thus, the sensor laminate 7 sequentially includes the thermochromic resin layer 3, the solar cell layer 2, and the thermochromic resin layer 3 in the thickness direction.

The temperature sensor 1 of the third embodiment includes the double surface-type solar cell layer 2, so that the electric power generation per unit area of the solar cell layer 2 is higher than that of the temperature sensor 1 of the first embodiment (ref: FIG. 1) including the one surface-type solar cell layer 2.

The temperature sensor 1 is preferably used in an air conditioning facility, more preferably used in a heating facility of a structure of cultivation in greenhouse.

When the temperature sensor 1 is used in the heating facility of the structure of the cultivation in greenhouse, the growth of cultivated plants is easily interrupted by a shadow produced by the temperature sensor 1. Alternatively, in the temperature sensor 1 of the third embodiment, the electric power generation per unit area of the solar cell layer 2 is high, so that when the area of the solar cell layer 2 is reduced, and the interruption of the growth of the cultivated plants is suppressed, the electric power generation of the solar cell layer 2 can be retained.

7. Fourth Embodiment

In the fourth embodiment, the same reference numerals are provided for members and steps corresponding to each of those in the first to third embodiments, and their detailed description is omitted.

Figure 4:
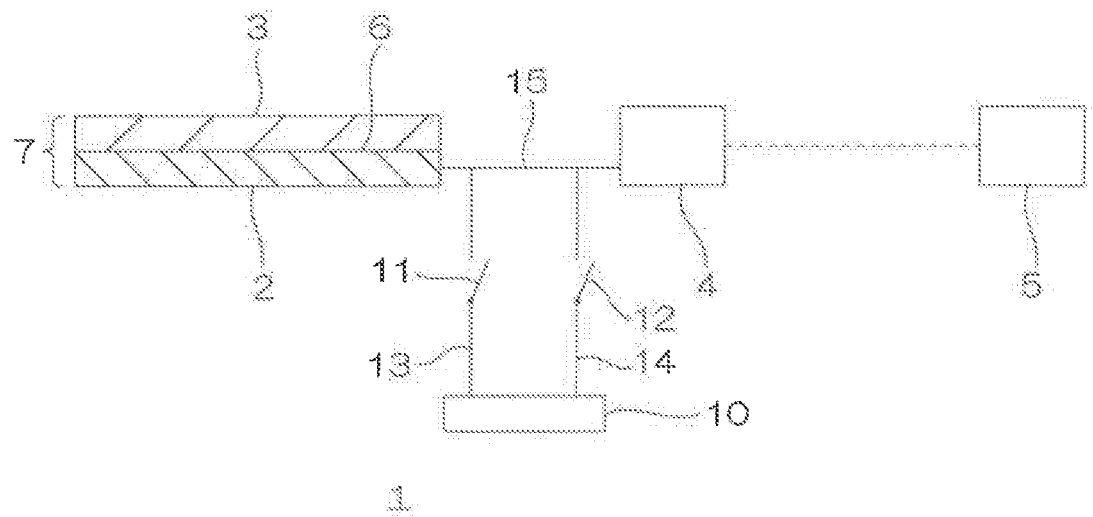
FIG. 4 shows a schematic view of a fourth embodiment of a temperature sensor of the present invention.

As shown in FIG. 4, the fourth embodiment includes a secondary cell 10 that is connected to the solar cell layer 2 and the transmitter 4 via the first wire 15, a first branch wire 13 and a second branch wire 14 that branch off from the first wire 15, and a first switch 11 and a second switch 12 that are interposed in the first branch wire 13 and the second branch wire 14, respectively.

Each of the first branch wire 13 and the second branch wire 14 branches off from two places between the solar cell layer 2 and the transmitter 4 of the first wire 15. A branching point of the first branch wire 13 in the first wire 15 is positioned at the upper stream side in a flowing direction of the electric current with respect to that of the second branch wire 14 in the first wire 15. Both of the first branch wire 13 and the second branch wire 14 are connected to the secondary cell 10. In the first branch wire 13, the first switch 11 is provided. In the second branch wire 14, the second switch 12 is provided.

In the fourth embodiment, when the solar cell layer 2 generates electricity, the first switch 11 is closed, and the second switch 12 is opened. Then, the secondary cell 10 accumulates the electricity generated in the solar cell layer 2.

Meanwhile, when the secondary cell 10 discharges electricity, the first switch 11 is opened, and the second switch 12 is closed. Then, the transmitter 4 detects the electromotive force generated in the solar cell layer 2 only as a signal. The transmitter 4, for example, amplifies the signal based on the discharge of the electricity of the secondary cell 10 based on the detected signal.

Furthermore, the secondary cell 10 is connected to another electrical device (not shown) via another wire (not shown), and the other electrical device (not shown) can be also operated with the secondary cell 10 as a power source.

Preferably, as in the first embodiment of FIG. 1, the temperature sensor 1 does not include the secondary cell 10, the first switch 11, and the second switch 12.

8. Modified Example of Fourth Embodiment

In the fourth embodiment, as shown in FIG. 4, the secondary cell 10 is connected to the first wire 15 via the first branch wire 13 and the second branch wire 14.

Figure 5:
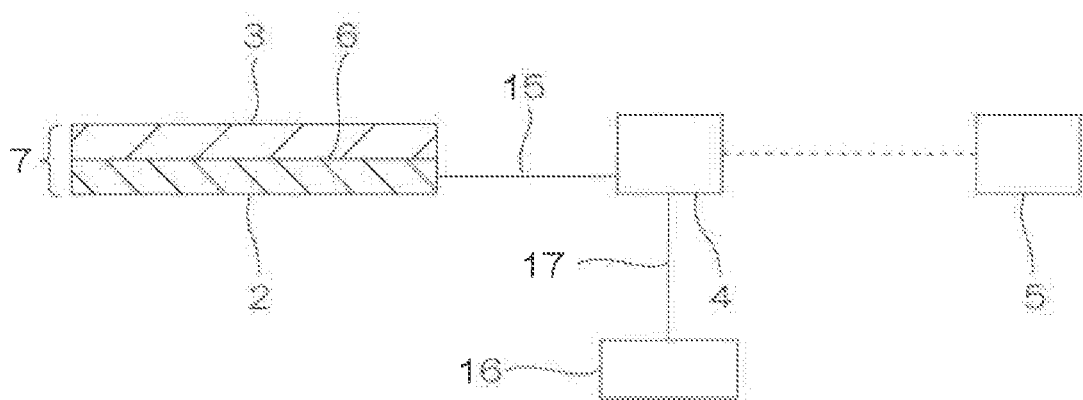
FIG. 5 shows a schematic view of a modified example of the fourth embodiment shown in FIG. 4.

Alternatively, as shown in FIG. 5, an external power source 16 can be connected to the transmitter 4 via an electric power supply wire 17 without using the first wire 15.

The external power source 16 is electrically connected to the transmitter 4 by the electric power supply wire 17. The external power source 16 includes, for example, a first cell, a secondary cell, or the like.

In the modified example, the transmitter 4 only detects the electromotive force generated in the solar cell layer 2. The transmitter 4 is operated by the electric power supplied from the external power source 16. That is, the transmitter 4 only detects the electromotive force generated in the solar cell layer 2. The transmitter 4 amplifies, for example, the signal by using the electric power supplied from the external power source 16 based on the detected signal.

9. Fifth Embodiment

In the first embodiment, as shown by a dotted line of FIG. 1, the transmitter 4 is constituted to wirelessly transmit a detected signal to the receiver 5.

Figure 6:
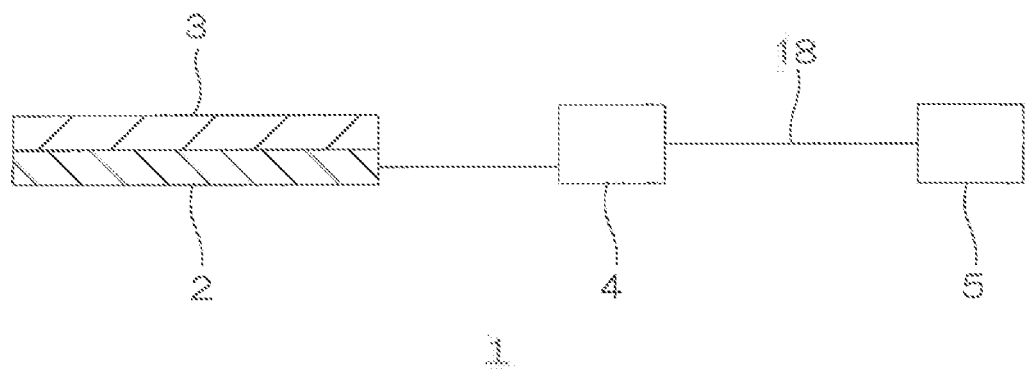
FIG. 6 shows a schematic view of a fifth embodiment of a temperature sensor of the present invention.

Alternatively, as shown in FIG. 6, in the fifth embodiment, the transmitter 4 is constituted to wire-transmit a detected signal to the receiver 5.

To be specific, the transmitter 4 is electrically connected to the receiver 5 by a signal wire 18.

When the solar cell layer 2 generates electricity, the transmitter 4 wire-transmits the detected signal with respect to the receiver 5 based on the electromotive force thereof.

According to the fifth embodiment, the transmitter 4 wire-transmits the detected signal to the receiver 5, so that the transmission can be surely achieved compared to the first embodiment (ref: FIG. 4) in which the transmitter 4 wirelessly transmits the signal to the receiver 5.

Meanwhile, in the first embodiment, the receiver 5 can be disposed remotely with respect to the transmitter 4, so that a degree of freedom of the placement of the receiver 5 can be increased.

10. Sixth Embodiment

In the sixth embodiment, the same reference numerals are provided for members and steps corresponding to each of those in the first to fourth embodiments, and their detailed description is omitted.

In the fifth embodiment, as shown in FIG. 6, the temperature sensor 1 includes the transmitter 4.

Figure 7:
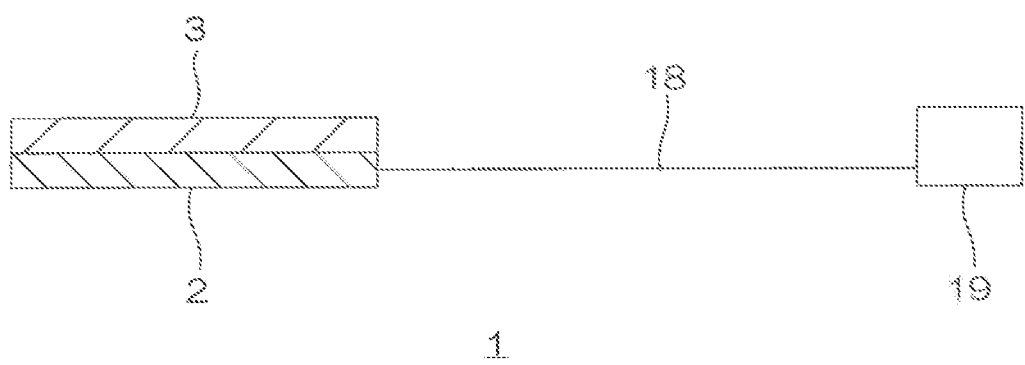
FIG. 7 shows a schematic view of a sixth embodiment of a temperature sensor of the present invention.

Alternatively, as shown in FIG. 7, in the sixth embodiment, the temperature sensor 1 does not include the transmitter 4, and includes the solar cell layer 2, the thermochromic resin layer 3, and the signal wire 18.

The signal wire 18 electrically connects the solar cell layer 2 to a trigger switch 19 that is provided separately from the temperature sensor 1.

The trigger switch 19 is a switch that turns on or turns off an air conditioning facility, when the temperature sensor 1 is, for example, provided in the air conditioning facility.

When the electromotive force is generated in the solar cell layer 2, the electromotive force is transmitted to the trigger switch 19 as a trigger signal, and the trigger switch 19 either turns on or turns off the air conditioning facility (heating facility).

In the sixth embodiment, the temperature sensor 1 does not include the transmitter 4 and the receiver 5, so that the number of components is reduced, and the structure can be simplified.

EXAMPLES

The specific numerical values in mixing ratio (content ratio), property value, and parameter used in the following description can be replaced with upper limit values (numerical values defined as "or less" or "below") or lower limit values (numerical values defined as "or more" or "above") of corresponding numerical values in mixing ratio (content ratio), property value, and parameter described in the above-described "DESCRIPTION OF EMBODIMENTS".

All designations of "part" or "parts" and "%" mean part or parts by mass and % by mass, respectively, unless otherwise particularly specified in the following description.

Example 1

As shown in FIG. 1, the temperature sensor 1 including the sensor laminate 7 that was made of the solar cell layer 2 and the thermochromic resin layer 3, and the electric power detecting portion 4 that was electrically connected to the solar cell layer 2 was prepared.

The thermochromic resin layer 3 was prepared from a silicone resin and a thermochromic pigment (color changing point: 30° C.). Furthermore, the electric power detecting portion 4 included a voltammeter and a rectifier. Each of the members described above is shown in Table 1. The mixing ratio of the silicone resin and the thermochromic pigment is shown in Table 2.

Next, the solar cell layer 2 of the sensor laminate 7 was brought into contact with a heating device (SHAMAL HOTPLATE, product number: HHP-411, manufactured by AS ONE Corporation) at 25° C. (non-operating state). Next, light was applied to the thermochromic resin layer 3 of the sensor laminate 7 at an illuminance of 500 lux. The electric voltage and the electric current detected in the electric power detecting portion 4 were measured, and the electric power was measured based on the obtained values.

Next, the electric voltage and the electric current detected in the electric power detecting portion 4 at the time of increasing the temperature of the above-described heating device to 35° C. were measured, and the electric power was measured based on the obtained values.

The results are shown in Table 2.

As is clear in Table 2, in Example 1, the electric power detecting portion 4 could detect an increase in the electric power in the thermochromic resin layer 3, so that it was found that the temperature of the heating device detected the temperature T (color changing point of the thermochromic material) or more in the thermochromic resin layer 3.

Examples 2 and 3

The treatment was performed in the same manner as in Example 1, except that the mixing ratio of the thermochromic pigment, the thickness of the thermochromic resin layer, and the illuminance were changed to those described in Table 2.

The results are shown in Table 2.

As is clear in Table 2, in Examples 2 and 3, the electric power detecting portion 4 could detect an increase in the electric power in the thermochromic resin layer 3, so that it was found that the temperature of the heating device detected the temperature T (color changing point of the thermochromic material) or more in the thermochromic resin layer 3.

TABLE 1

| Member Material | | Product Name | Product Number | Manufacturer |
|---|---|---|---|---|
| Solar Cell Layer | Solar Cell | Amorton Film | AAT-7665 | Panasonic Eco Solutions Amorton Co. LTD. |
| Thermochromic Resin Layer | Silicone Resin | KE-109E-A | — | Shin-Etsu Chemical Co. Ltd. |
| | | KE-109E-B | — | Shin-Etsu Chemical Co. Ltd. |
| | Thermochromic Pigment | ETSD Powder | ETSD 30*1 | JAPAN CAPSULAR PRODUCTS INC. |
| Heating Device | | SHAMAL HOTPLATE | HHP-411 | AS ONE Corporation |
| Electric Power Detecting Portion | Voltammeter | DIGITAL MULTIMETER | R6552 | ADVANTEST CORPORATION |
| | Rectifier | Small Switching Type Constant Voltage Constant Current DC Power Source | KX-100H | TAKASAGO LTD. |

*3: Color Changing Point: 30° C.

TABLE 2

| | | Unit | Ex. 1 | | Ex. 2 | | Ex. 3 | |
|---|---|---|---|---|---|---|---|---|
| Solar Cell | Product Number | — | AT7665 | | AT76665 | | AT7665 | |
| Silicon Resin | Product Number | — | KE-109E-A | KE-109E-B | KE-109E-A | KE-109E-B | KE-109E-A | KE-109E-B |
| | Mixing Ratio | parts | 50 | 50 | 50 | 50 | 50 | 50 |
| Thermochromic Pigment | Product Number | — | ETSD30*3 | | ETSD30*3 | | ETSD30*3 | |
| Mixing Ratio of Thermochromic Pigment (vs 100 parts of Silicone Resin) | | parts | 7.5 | | 5 | | 5 | |
| Thickness of Thermochromic Resin Layer | | μm | 30 | | 100 | | 100 | |
| Illuminance | Placement Point | lux | 500 | | 500 | | 900 | |
| Temperature of Heating Device | | ° C. | 25 | 35 | 25 | 35 | 25 | 35 |
| Evaluation | Electric Voltage | V | 2.8 | 2.8 | 2.3 | 2.3 | 2.5 | 2.6 |
| | Electric Current | μA | 80.9 | 106.1 | 21.8 | 65.2 | 42.7 | 112.6 |
| | Electric Power | μW | 226.5 | 297.1 | 50.1 | 150.0 | 106.8 | 292.8 |
| | Difference of Electric Current*1 | μA | 25.2 | | 43.4 | | 69.9 | |
| | Difference of Electric Power*2 | μW | 70.6 | | 99.8 | | 186.0 | |

Difference of Electric Current*1: [Electric Current at 35° C.] − [Electric Current at 25° C.]

Difference of Electric Power*2: [Electric Power at 35° C.] − [Electric Power at 25° C.]

*3Color Changing Point: 30° C.

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

INDUSTRIAL APPLICABILITY

The temperature sensor is used in an automatic fire alarm facility, an atmospheric temperature sensor, a patch, or the like.

DESCRIPTION OF REFERENCE NUMERALS

1 Temperature sensor
2 Solar cell layer
3 Thermochromic resin layer
4 Transmitter (electric power detecting portion)

The invention claimed is:

1. A patch comprising:
a temperature sensor, wherein
the temperature sensor comprises:
   a solar cell, and
   a thermochromic resin covering the solar cell and having a light transmittance changeable according to a temperature change.

2. The patch according to claim 1, wherein
the thermochromic resin is in direct contact with the solar cell.

3. The patch according to claim 1, wherein
each of the thermochromic resin and the solar cell has a film shape, and
the thermochromic resin is disposed at one side in a thickness direction of the solar cell.

4. The patch according to claim 1 further comprising:
an electric power detecting portion electrically connected to the solar cell and detecting an electromotive force generated in the solar cell.

5. The patch according to claim 4, wherein
the electric power detecting portion is operated by an electric power directly supplied from the solar cell.

6. The patch according to claim 4 further comprising:
a transmitting device connected to the solar cell, wherein
the electric power detecting portion is the transmitting device.

7. The patch according to claim 1, wherein the thermochromic resin includes a thermochromic pigment.

8. The patch according to claim 1, further comprising:
a patch layer disposed on a surface of the temperature sensor, wherein
the patch layer contains a patch medicinal component and has pressure-sensitive adhesive properties.

* * * * *